(12) United States Patent
McCollam

(10) Patent No.: US 8,968,347 B2
(45) Date of Patent: Mar. 3, 2015

(54) DUAL-MODE ILLUMINATION FOR SURGICAL INSTRUMENT

(75) Inventor: Christopher L. McCollam, Lake Forest, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 295 days.

(21) Appl. No.: 13/207,092

(22) Filed: Aug. 10, 2011

(65) Prior Publication Data
US 2012/0041461 A1 Feb. 16, 2012

Related U.S. Application Data

(60) Provisional application No. 61/373,575, filed on Aug. 13, 2010.

(51) Int. Cl.
| A61B 17/32 | (2006.01) |
| A61F 9/007 | (2006.01) |
| A61B 19/00 | (2006.01) |
| A61F 9/008 | (2006.01) |

(52) U.S. Cl.
CPC ......... A61F 9/00736 (2013.01); A61B 19/5202 (2013.01); *A61B 2019/5206* (2013.01); *A61B 2019/521* (2013.01); *A61F 9/00821* (2013.01); *A61F 2009/00874* (2013.01)
USPC .......................................................... 606/170

(58) Field of Classification Search
USPC ................ 606/4, 15, 16, 167, 170, 171, 185; 604/20; 600/178; 351/221; 359/385
See application file for complete search history.

(56) References Cited

U.S. PATENT DOCUMENTS

| 4,607,622 | A | | 8/1986 | Fritch et al. | |
| 5,217,456 | A | * | 6/1993 | Narciso, Jr. | 606/15 |
| 5,263,952 | A | * | 11/1993 | Grace et al. | 606/15 |
| 5,312,393 | A | * | 5/1994 | Mastel | 606/4 |
| 5,754,717 | A | * | 5/1998 | Esch | 385/31 |
| 6,080,143 | A | | 6/2000 | Connor | |
| 2005/0154379 | A1 | | 7/2005 | McGowan, Sr. et al. | |
| 2005/0245916 | A1 | * | 11/2005 | Connor | 606/4 |
| 2008/0108981 | A1 | * | 5/2008 | Telfair et al. | 606/4 |
| 2008/0147018 | A1 | | 6/2008 | Squilla et al. | |
| 2009/0135280 | A1 | | 5/2009 | Johnston et al. | |
| 2009/0163897 | A1 | | 6/2009 | Skinner | |
| 2009/0182313 | A1 | | 7/2009 | Auld | |

OTHER PUBLICATIONS

Fisher, MD. et al; "Inexpensive Illuminated Vitrectomy Cutter"; Retina; Dec. 2003; 23(6):891.
Chalam, MD. et al; "Illuminated curved 25-gauge vitrectomy probe for removal of subsclerotomy vitreous in vitreoretinal surgery"; Indian J. Ophthalmol.; Jul.-Aug. 2008; 56(4):331-34.
European Search Report, EP11816989.5, European Searching Authority, Oct. 16, 2013, 8pgs.

* cited by examiner

*Primary Examiner* — Katherine M Shi
(74) *Attorney, Agent, or Firm* — Jason Finch

(57) ABSTRACT

An illuminated surgical instrument is disclosed. One embodiment of the present invention comprises an illuminated vitrectomy probe. The vitrectomy probe has a cutting port disposed at a distal end of a cannula. An array of optical fibers terminates near the cutting port. The array of optical fibers is located adjacent to the cannula and encircling the cannula. The array of optical fibers can comprise two sets of fibers, one for providing illumination in a direction along a longitudinal axis of the vitrectomy probe and another for providing illumination in a direction at an angle to the longitudinal direction of the vitrectomy probe. The light source providing light to each set of fibers can be independently controlled so as to provide illumination cooperatively or singly.

19 Claims, 4 Drawing Sheets

DUAL-MODE ILLUMINATION FOR SURGICAL INSTRUMENT

This application claims priority to U.S. Provisional Patent Application Ser. No. 61/373,575 filed on Aug. 13, 2010, the entire contents of which are incorporated herein.

BACKGROUND OF THE INVENTION

The present invention relates to an illuminated vitrectomy probe or other illuminated ophthalmic surgical instrument, and more particularly to an optical fiber array configuration designed to provide illumination over a specific area at the working end of an instrument, for example, the cutting port of a vitrectomy probe.

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, to maintain the integrity and shape of the globe, to absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body (such as a vitrectomy probe—which has a cutting end that is inserted into the eye. A vitrectomy probe has a small gauge needle or cannula with a cutting mechanism on the end that is inserted into the eye).

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is launched at an optical fiber that carries the light into the eye.

To reduce the number of required incisions during vitrectomy surgery and improve the delivery of light to the surgical site, an effort has been made to integrate a light source (typically one or more optical fibers) with a vitrectomy probe. These efforts have been difficult because of the small diameters of vitrectomy probes. It is desirable to make the diameter of the cutting end of the vitrectomy probe as small as possible so that it can be inserted through very small incisions into the eye.

In one case, a ring of optical fibers is disposed around a vitrectomy probe and held in place by a sleeve. This illuminated vitrectomy sleeve consists of a bundle of small diameter optical fibers fed into a hub region and then distributed in a ring pattern. The illuminated vitrectomy sleeve is designed to be a stand-alone device into which the vitrectomy probe is inserted. As such, it must have its own structural strength that is provided by a sandwiching the array of optical fibers between two metal or plastic cylindrical cannulas. Since it is preferable to make the total diameter of the vitrectomy probe and sleeve as small as possible, very little cross-sectional area is left to house the optical fibers. Accordingly, very little light is transmitted into the eye. In addition, the ring of fibers distributes light throughout the entire region adjacent to the distal end of the vitrectomy probe instead of concentrating it on the cutting port opening where it is needed.

In another case, a single fiber may be attached to the vitrectomy needle and held in place with a plastic sleeve. For example, Synergetics, Inc. manufactures a 25-gauge vitrectomy needle with a single optical fiber that is held in place with a plastic sleeve. The plastic sleeve can then fit into a 20-gauge cannula that is inserted into the eye. Very little cross-sectional area is available between the 25-gauge vitrectomy needle and the inner surface of the plastic sleeve (which is typically one or two mils thick). In addition, a larger incision must be made to accommodate the 20-gauge cannula through which the plastic sleeve must fit. Today, it is preferable to keep the incision size small so as to accommodate a probe with a diameter of 23-gauge or smaller. What is needed is an improved illuminated vitrectomy probe that delivers sufficient light into the eye while accommodating these smaller incision sizes.

Further, both end illumination (along a probe cannula longitudinal axis) and/or angle illumination (e.g., at an angle to the cannula longitudinal axis) may be useful when combined with a vitrectomy probe or other ophthalmic instrument, for example, to eliminate the need for a separate and additional instrument to provide side (angle) illumination. Known illumination devices, such as those described above, can provide end illumination, though with deficiencies as noted, but there are no available devices that combine end and side illumination, and the ability to provide one or the other or both, in a small diameter instrument. It would likewise be desirable to also combine, in a same or similarly-sized vitrectomy probe, endolaser capability for performing cauterizing-type procedures on the retina.

The same constraints described above also restrict the feasible size of other ophthalmic surgical instruments. For example, scissors, forceps, aspiration probes, retinal picks, delamination spatulas, various cannulas, and the like may also benefit from targeted illumination. These instruments are designed to fit through small gauge cannulas that are inserted through the sclera during surgery. The same principles used to design an improved illuminated vitrectomy probe can also be used to provide targeted illumination for these other surgical instruments.

SUMMARY OF THE INVENTION

One embodiment of the present invention comprises an illuminated vitrectomy probe. The vitrectomy probe has a cutting port disposed at a distal end of a cannula. An array of optical fibers terminates near the cutting port. The array of optical fibers is located adjacent to the cannula and encircling the cannula. The array of optical fibers can comprise two sets of fibers, one for providing illumination in a direction along a longitudinal axis of the vitrectomy probe and another for providing illumination in a direction at an angle to the longitudinal direction of the vitrectomy probe. The light source providing light to each set of fibers can be independently controlled so as to provide illumination cooperatively or singly.

In another embodiment consistent with the principles of the present invention, the present invention is an illuminated vitrectomy probe with endolaser capability. The vitrectomy probe has a cutting port disposed at a distal end of a cannula. An endolaser fiber runs coaxially through the interior of the cannula and terminates at the distal end of the cannula. The endolaser fiber is optically connected at its proximal end to a laser light source. An array of optical fibers terminates near the cutting port. The array of optical fibers is located adjacent to the cannula and encircling the cannula. The array of optical fibers can comprise two sets of fibers, one for providing illumination in a direction along a longitudinal axis of the vitrectomy probe and another for providing illumination in a direction at an angle to the longitudinal direction of the vitrectomy probe. The light source providing light to each set of fibers, and the endolaser light source, can each be independently controlled so as to provide illumination and laser light cooperatively or singly.

In another embodiment consistent with the principles of the present invention, the present invention is an illuminated surgical instrument. The instrument has a working area located near an end of the instrument. An array of optical fibers terminates near the end of the instrument. The array of optical fibers is located adjacent to the instrument and can comprise two sets of fibers, one for providing illumination in a direction along a longitudinal axis of the instrument and another for providing illumination in a direction at an angle to the longitudinal direction of the instrument. The light source providing light to each set of fibers can be independently controlled so as to provide illumination cooperatively or singly. The surgical instrument can also have endolaser capability as described above.

In another embodiment consistent with the principles of the present invention, the present invention is an illuminated surgical instrument. The instrument has a working area located near an end of the instrument. The working area has an orientation with respect to the end of the instrument. An array of optical fibers terminates near the end of the instrument. The array of optical fibers is located adjacent to the instrument and can comprise two sets of fibers, one for providing illumination in a direction along a longitudinal axis of the instrument and another for providing illumination in a direction at an angle to the longitudinal direction of the instrument. The light source providing light to each set of fibers can be independently controlled so as to provide illumination cooperatively or singly. The targeted illumination is configured for the orientation of the working area. The surgical instrument can also have endolaser capability as described above.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
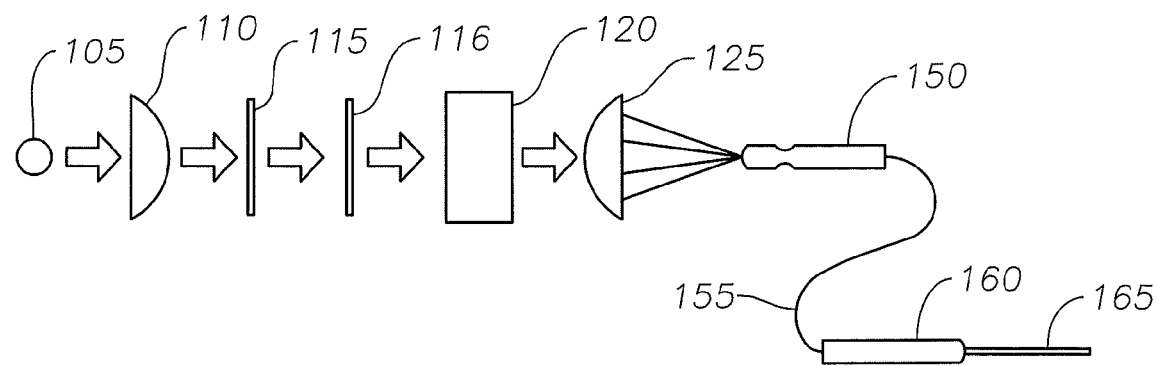
FIG. 1 is an unfolded view of an ophthalmic endoilluminator according to an embodiment of the present invention.

FIG. 1 is an unfolded view of an exemplary ophthalmic endoilluminator as used with an illuminated vitrectomy probe according to an embodiment of the present invention. In FIG. 1, the endoilluminator includes light source 105, collimating lens 110, optional cold mirror 115, optional hot mirror 116, attenuator 120, condensing lens 125, connector 150, optical fiber 155, hand piece 160, and vitrectomy probe 165.

The light from light source 105 is collimated by collimating lens 110. The collimated light is reflected and filtered by optional cold mirror 115 and/or transmitted and filtered by optional hot mirror 116. The resulting beam is attenuated by attenuator 120 and focused by condensing lens 125. The focused beam is directed through connector 150 and optical fiber 155 to vitrectomy probe 165 where it illuminates the inside of the eye as described below.

Light source 105 is typically a lamp, such as a mercury vapor lamp, a xenon lamp, a metal halide lamp, or a halogen lamp. Light source 105 is operated at or near full power to produce a relatively stable and constant light output. In one embodiment of the present invention, light source 105 is a xenon lamp with an arc length of about 0.18 mm. Other embodiments of the present invention utilize other light sources such as light emitting diodes (LEDs). One or more LEDs can be operated to produce a constant and stable light output. As is known, there are many types of LEDs with different power ratings and light output that can be selected as light source 105.

Collimating lens 110 is configured to collimate the light produced by light source 105. As is commonly known, collimation of light involves lining up light rays. Collimated light is light whose rays are parallel with a planar wave front.

Optional cold mirror 115 is a dichroic reflector that reflects visible wavelength light and only transmits infrared and ultraviolet light to produce a beam filtered of harmful infrared and ultraviolet rays. Optional hot mirror 116 reflects long wavelength infrared light and short wavelength ultraviolet light while transmitting visible light. The eye's natural lens filters the light that enters the eye. In particular, the natural lens absorbs blue and ultraviolet light which can damage the retina. Providing light of the proper range of visible light wavelengths while filtering out harmful short and long wavelengths can greatly reduce the risk of damage to the retina through aphakic hazard, blue light photochemical retinal damage and infrared heating damage, and similar light toxicity hazards. Typically, a light in the range of about 430 to 700 nanometers is preferable for reducing the risks of these hazards. Optional cold mirror 115 and optional hot mirror 116 are selected to allow light of a suitable wavelength to be emitted into an eye. Other filters and/or dichroic beam splitters may also be employed to produce a light in this suitable wavelength range. For example, holographic mirrors may also be used to filter light.

Attenuator 120 attenuates or decreases the intensity of the light beam. Any number of different attenuators may be used. For example, mechanical louvers, camera variable aperture mechanisms, or neutral density filters may be used. A variable-wedge rotating disk attenuator may also be used.

Condensing lens 125 focuses the attenuated light beam so that it can be launched into a small diameter optical fiber. Condensing lens 125 is a lens of suitable configuration for the system. Condensing lens 125 is typically designed so that the resulting focused beam of light can be suitably launched into and transmitted by an optical fiber. As is commonly known, a condensing lens may be a biconvex or plano-convex spherical or aspheric lens. In a plano-convex aspheric lens, one surface is planar and the other surface is convex with a precise aspheric surface in order to focus the light to a minimum diameter spot.

The endoilluminator that is handled by the ophthalmic surgeon includes connector 150, optical fiber 155, hand piece 160, and illuminated vitrectomy probe 165. Connector 150 is designed to connect the optical fiber 155 to a main console (not shown) containing light source 105. Connector 150 properly aligns optical fiber 155 with the beam of light that is to be transmitted into the eye. Optical fiber 155 is typically a small diameter fiber that may or may not be tapered. Hand piece 160 is held by the surgeon and allows for the manipulation of illuminated vitrectomy probe 165 in the eye.

Figure 8:
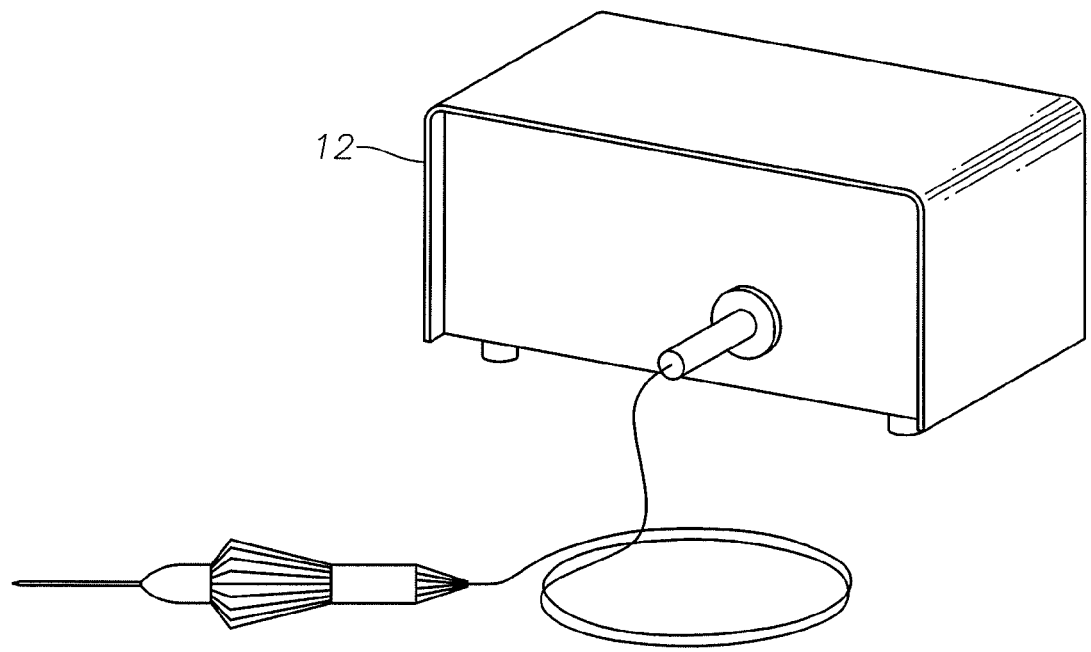
FIG. 8 is a diagrammatic representation of a laser light source for providing endolaser illumination for use with an illuminated surgical instrument according to an embodiment of the present invention.

Similar to the above and in a manner that will be known to those having skill in the art, a laser light source 12, such as shown in FIG. 8, can be optically connected to provide laser light to an endolaser fiber in those embodiments of the illuminated vitrectomy probe of the present invention that comprise an endolaser fiber to provide laser light to, for example, the retina. A laser light source 12 and an endoilluminator light source, such as described with reference to FIG. 1, can be combined into a single laser/illumination source optically coupled in a manner such as described herein via, for example, an optical cable having separate optical fibers terminating at the appropriate light source or the laser and illumination sources can be separate units, each coupled via independent cables to an illuminated vitrectomy probe or other surgical instrument in accordance with the teachings of the present invention.

Figure 2A:
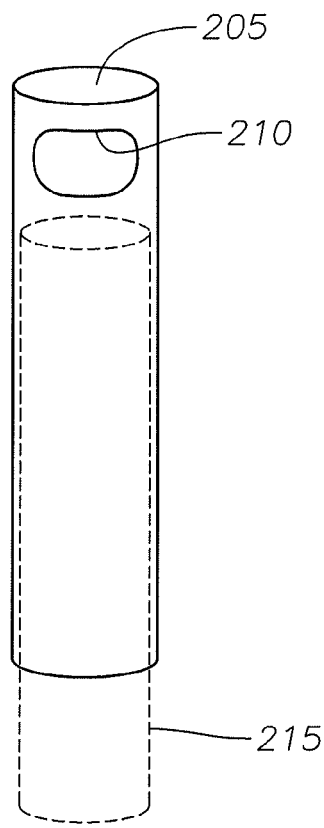
FIGS. 2A and 2B are perspective views of a vitrectomy probe according to an embodiment of the present invention.
Figure 2B:
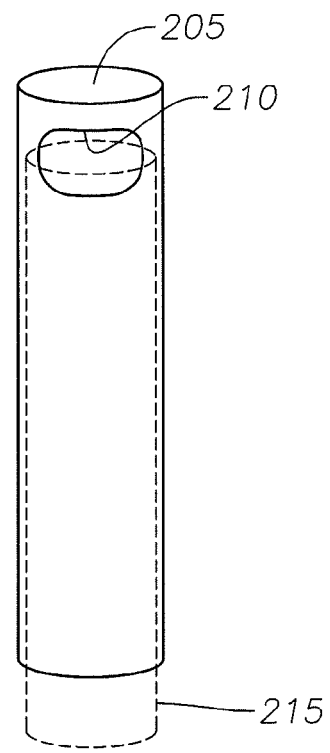

FIGS. 2A and 2B are perspective views of a vitrectomy probe according to an embodiment of the present invention. In a typical vitrectomy probe, an outer cannula 205 includes port 210. An inner piston 215 reciprocates in cannula 205. One end of piston 215 is configured so that it can cut vitreous when as it enters port 210. As shown in FIGS. 2A and 2B, piston 215 moves up and down in cannula 205 to produce a cutting action. Vitreous enters port 210 when the vitrectomy probe is in the position shown in FIG. 2A. The vitreous is cut as piston 215 moves upward closing off port 210 as shown in FIG. 2B. While most of the details of a vitrectomy probe are omitted, it is important to note that the cutting of the vitreous takes place at port 210. Accordingly, it would be desirable to concentrate illumination around port 210, so that a surgeon can see the vitreous being cut (as well as other eye structures near the cutting mechanism). Embodiments of the present invention can also comprise fibers to provide illumination at an angle to the longitudinal axis of the vitrectomy probe (e.g., normal to port 210 (perpendicular to the longitudinal axis of the vitrectomy probe)). Further, embodiments of the present invention can comprise an endolaser fiber running coaxially through the interior of inner piston 215 and cannula 205 and terminating at a distal end of cannula 205.

Figure 3A:
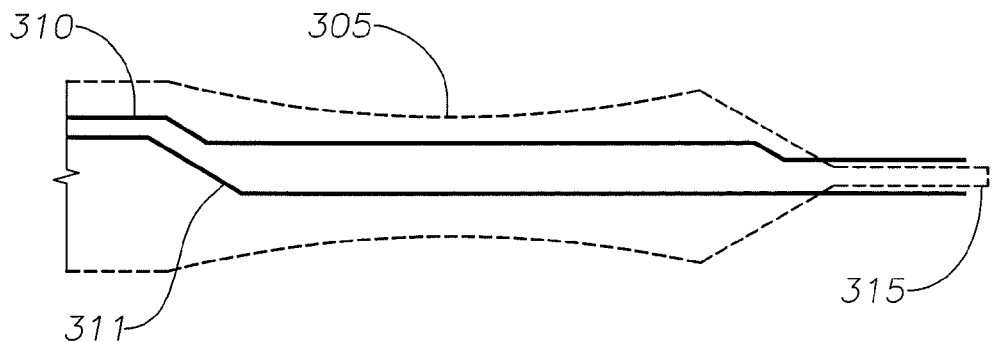
FIG. 3A is a cross section view of a vitrectomy hand piece with integrated illumination according to an embodiment of the present invention.

FIG. 3A is a cross section view of a vitrectomy hand piece with an integrated illuminator according to an embodiment of the present invention. In FIG. 3A, an end illumination array of optical fibers 310 and an angle illumination array of optical fibers 311 are located in vitrectomy hand piece housing 305. Optical fiber arrays 310/311 exit the hand piece housing 305 at a small opening adjacent to cannula 315. Cannula 315 can be similar in structure and operation to cannula 205 of FIGS. 2A and 2B. End illumination array optical fibers 310 emit light to provide illumination beyond the distal dip of cannula 205 in a direction along the longitudinal axis of cannula 205.

Figure 3B:
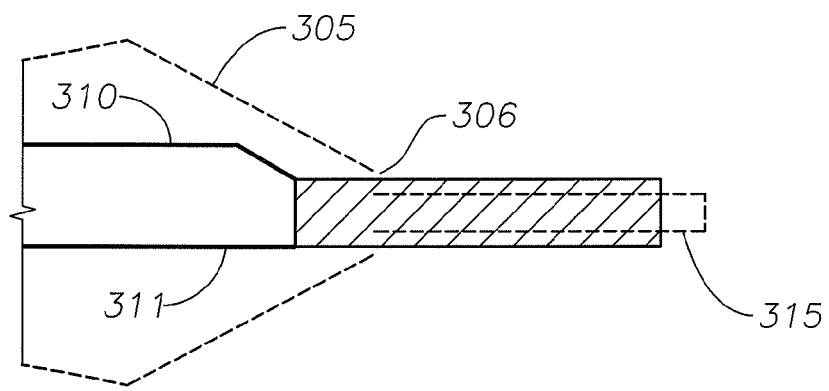
FIG. 3B is an exploded cross section view of a vitrectomy hand piece with integrated illumination according to an embodiment of the present invention.
Figure 5:
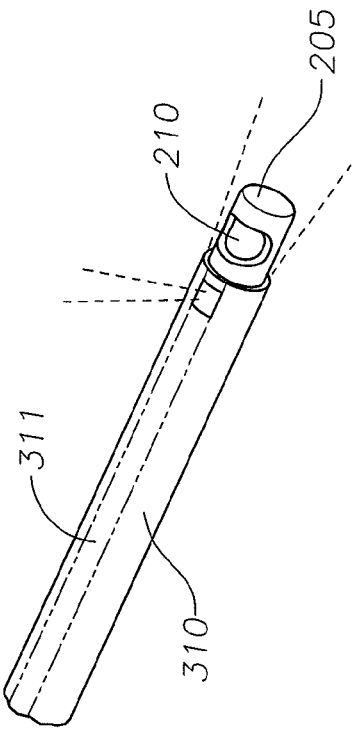
FIG. 5 is a perspective view of one embodiment of an illuminated vitrectomy probe in accordance with the present invention having end and angle illumination.
Figure 6:
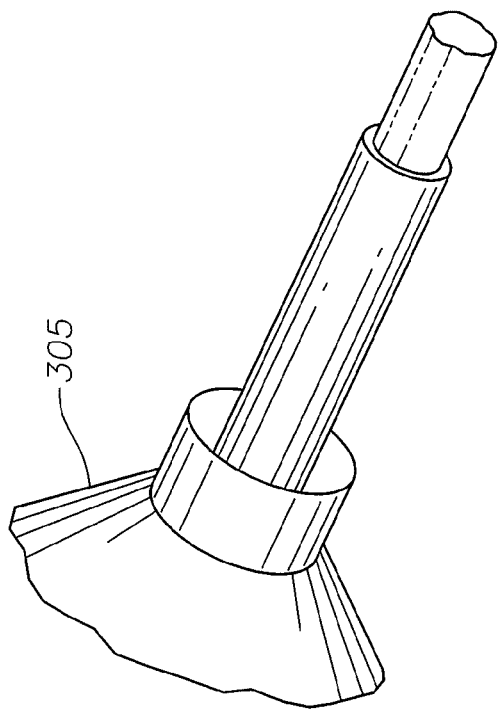
FIG. 6 is a blown-up view of an exemplary angle illumination array of optical fibers showing the apertures created to emit light at an angle to the longitudinal axis of a cannula in accordance with an embodiment of the present invention.
Figure 6:
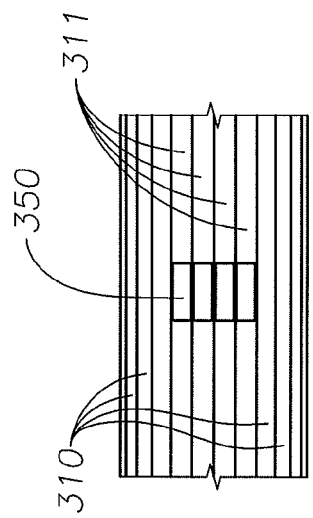
Figure 7:
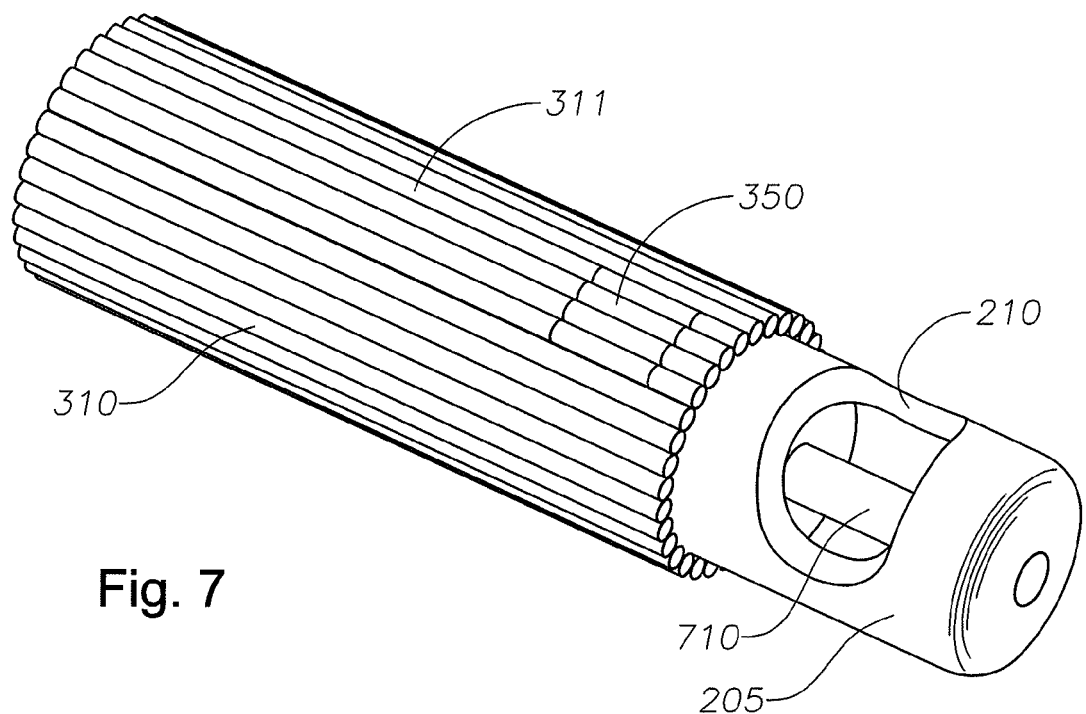
FIG. 7 is a perspective view of one embodiment of an illuminated vitrectomy probe in accordance with the present invention having end and angle illumination and endolaser capability.

FIG. 3B is an exploded cross section view of a vitrectomy hand piece with an integrated illuminator according to an embodiment of the present invention. FIG. 3B more clearly shows the orientation of optical fiber arrays 310/311 with respect to hand piece housing 305 and cannula 315. Optical fiber arrays 310/311 exit hand piece housing 305 through a small opening adjacent to cannula 315. Optical fiber arrays 310/311 are arranged at a distal end of cannula 315 as depicted in FIGS. 5-7. The small opening 306 in hand piece housing 305 through which optical fiber array 310 passes may be sealed.

Figure 4:
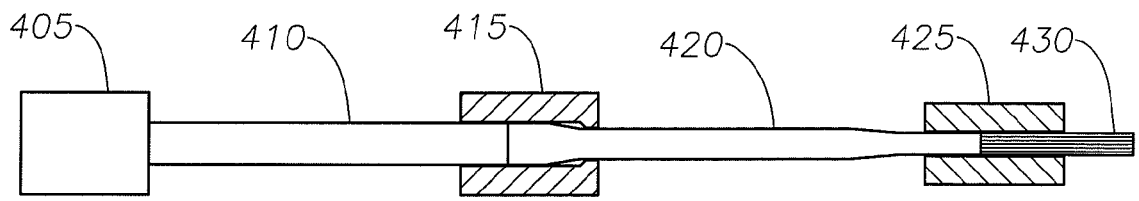
FIG. 4 is a cross section view of an illuminator optical fiber path according to an embodiment of the present invention.

FIG. 4 is cross section view of an illuminator optical fiber path according to an embodiment of the present invention. In the embodiment of FIG. 4, a standard 20-gauge ACMI connector 405 is coupled to a proximally belled 0.0295 inch, 0.5

NA or 0.63 NA optical fiber 410. Optical fiber 410 is coupled to a belled, stretched 0.63 NA optical fiber 420 via a 25-gauge coupling 415. A second coupling 425 couples optical fiber 420 to an array of optical fibers 430. While a specific example is provided in FIG. 4, numerous other configurations of optical fibers and couplers may be employed to implement the illuminated vitrectomy probe of the present invention.

FIG. 5 is a perspective view of one embodiment of an illuminated vitrectomy probe in accordance with the present invention having end and angle illumination. End illumination array of optical fibers 310 and an angle illumination array of optical fibers 311 are each routed through handpiece housing 305 and terminate at their distal end near port 210 of cannula 205. The optical fibers in each array can be embedded in a material, such as epoxy or other bio-compatible material, and attached to cannula 205 by, for example, a potting substance, or can be secured to cannula 205 by, for example, a sleeve such as metal or shrink tubing. As can be seen in FIGS. 5-7, end illumination array 310 and angle illumination array 311 are arranged circumferentially around cannula 205 such that they are adjacent to and together completely encircle cannula 205. However, embodiments of the illuminated surgical instrument of this invention can comprise arrays 310 and 311 that do not completely encircle cannula 205 and the ratio of fibers in arrays 310 and 311 can vary as desired for a particular application. The ratio shown in FIGS. 5 and 7 is roughly 9 to 1—i.e., for every 9 end illumination optical fibers there is one angle illumination optical fiber, but this ratio is exemplary only.

End illumination array 310 and angle illumination array 311 can operate in separately controllable modes. For example, in one mode, illumination light can be provided from a light source only to end illumination array 310 to emit light in the general direction of the cannula 205 longitudinal axis. In another mode, illumination light from a light source can be provided only to angle illumination array 311 to emit light in a direction at a chosen angle to the longitudinal axis of cannula 205. For example, angle illumination array optical fibers 311 can be configured to emit light in a direction perpendicular to the longitudinal axis of cannula 205 or at any other pre-determined angle as desired for a particular application. In still another mode, light can be provided to both end illumination array optical fibers 310 and angle illumination array optical fibers 311 simultaneously to emit light to provide illumination along both the general direction of the longitudinal axis of cannula 205 and at an angle to the longitudinal axis of cannula 205.

As is more clearly shown in FIGS. 6 and 7, angle illumination array optical fibers 311 comprise a set of apertures to emit light at an angle to the longitudinal axis of cannula 205. These apertures can be created by, for example, selectively removing the cladding from the optical fibers of angle illumination array optical fibers 311 at a desired location and in a desired configuration to obtain a desired angle of light emission. The distal ends of angle illumination array optical fibers 311 can be covered to prevent light emission from the distal ends.

End illumination array optical fibers 310 and angle illumination array optical fibers 311 can be routed through handpiece housing 305 and terminated separately. The proximal ends of each array can be terminated and secured in an appropriate connecting device appropriate for a selected illumination light source. The light delivered to each array can be separately controllable. For example, a single light source can provide light for both arrays and appropriate shutters or other light blocking devices can be used to control the delivery of light to each array. Alternatively, a separate independently controllable light source can be used to provide light to each array. In this way, either end illumination, angle (side) illumination or both can be provided to an illuminated vitrectomy probe, or other surgical instrument, in accordance with the teachings of this invention.

FIG. 7 is a perspective view of one embodiment of an illuminated vitrectomy probe in accordance with the present invention having end and angle illumination and endolaser capability. Endolaser light is provided from a laser light source such as light source 12 of FIG. 8 to a separate endolaser optical fiber 710. Endolaser optical fiber 710 runs coaxially through handpiece housing 305 and cannula 205, terminating distally at the distal tip of cannula 205. Endolaser optical fiber 710 is routed through handpiece housing 305 and terminates at its proximal end at an appropriate laser optical connector, as will be known to those having skill in the art, for connection to laser light source 12. Laser light source 12 can be independently operated so that laser light can be provided to endolaser optical fiber 710 either alone or in combination with illumination light to end illumination array 310 and/or angle illumination array 311. In this way, embodiments of the illuminated surgical instrument of the present invention can provide six different combinations of laser light and/or illumination light to a surgical site.

Embodiments of the present invention can have probe tip diameters (cannula and illumination arrays 310/311) such that the probe is a 25-gauge probe—that is, its cannula is a 25-gauge cannula. The probe tip can thus pass through, for example, a 23-gauge trocar cannula in order to enter the eye. In this manner, the vitrectomy cutting function and the illumination function—both of which are required for surgery—are provided in a small diameter package that can fit through a 23-gauge cannula. This small 23-gauge trocar cannula is desirable because smaller incision sizes in the eye generally result in fewer complications. In the same manner, a probe embodiment of the present invention having endolaser capability can pass through the same 23-gauge trocar cannula.

While the examples provided herein describe an illuminated vitrectomy probe that fits through a 23-gauge cannula, it will be appreciated that the same arrangement of a vitrectomy probe and optical fiber array can be applied to cannulas of other sizes. For example, optical fiber arrays can be arranged around a vitrectomy probe in the same way described herein to fit through a 20-gauge cannula, or even through cannulas smaller than 23-gauge. For example, as the diameter of a vitrectomy probe decreases, more cross section area is available for illumination. An illuminated vitrectomy probe that fits through a 25-gauge cannula can have the same optical fiber array configuration described herein.

More generally, the same principles described with respect to the illuminated vitrectomy probe of the preceding figures can be applied to any surgical instrument designed to fit through a small gauge cannula. For example, in ophthalmic surgery, scissors, forceps, aspiration probes, retinal picks, delamination spatulas, various cannulas, and the like may also benefit from targeted illumination. These instruments are designed to fit through small gauge cannulas that are inserted through the sclera during ophthalmic surgery. For each of these instruments, targeted illumination around the working end of the instrument is beneficial.

The same or similar arrangement of optical fibers (e.g., arrays 310 and 311) can be applied to any surgical instrument with a generally circular, elliptical, rectangular or other cross-section. In this manner, illumination can be targeted to a certain area (typically the working end of the instrument considering the orientation of the instrument in the eye) to provide light where it is needed. For example, in ophthalmic surgery, scissors, forceps, aspiration probes, retinal picks, delamination spatulas, various cannulas, and the like may benefit from targeted illumination. Providing light to the working area of the instrument or to the eye structure with which the instrument interfaces allows the surgeon to better see during surgery.

The same principles can be applied to an instrument of any cross section. In addition, instruments may be approximated by geometrical shapes. For example, an instrument that has an oblong cross section can be approximated by an ellipse. Of course, the location of the targeted illumination corresponds to the location of the optical fibers. While the fibers are generally selected to maximize light throughput, their location can be adjusted for a given instrument. Further, while the optical fibers are depicted as having a generally circular cross section, optical fibers and light guides with other cross sections may also be employed.

From the above, it may be appreciated that the present invention provides an improved illuminated vitrectomy probe. Arranging an array of optical fibers near the working area of a surgical instrument provides light that is usable by the surgeon during surgery. In addition, the present invention most effectively utilizes the small cross sectional area available to carry an optical fiber array. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An illuminated vitrectomy probe comprising:
   a vitrectomy probe having a cutting port disposed at a distal end of a cannula; and
   an array of optical fibers terminating near the cutting port, the array of optical fibers located adjacent to the cannula and arranged circumferentially around the cannula to encircle the cannula, the array of optical fibers comprising:
      an end-illumination array of optical fibers configured to provide illumination in a direction along a longitudinal axis of the cannula; and
      an angle-illumination array of optical fibers, each fiber having a covered terminal distal end to prevent light emission from the terminal distal end, one or more of the fibers being free from cladding to form an aperture along the radial surface of the illuminated vitrectomy probe to allow light emission from the aperture in order to provide illumination in a direction at an angle to the longitudinal axis of the cannula, the illumination of the angle-illumination array being at an angle relative to the illumination of the end-illumination array.

2. The illuminated vitrectomy probe of claim 1, wherein the array of optical fibers and cannula are configured to fit through a trocar cannula with a size not greater than 23-gauge.

3. The illuminated vitrectomy probe of claim 1, further comprising:
   a potting substance that holds the optical fibers against the cannula of the vitrectomy probe.

4. The illuminated vitrectomy probe of claim 1, further comprising:
   a sleeve that holds the optical fibers against the cannula of the vitrectomy probe.

5. The illuminated vitrectomy probe of claim 1, further comprising:
   a housing having an opening through which the array of optical fibers passes, the housing attached to the cannula.

6. The illuminated vitrectomy probe of claim 1, further comprising an endolaser fiber configured to provide laser light from a laser light source to a surgical site.

7. The illuminated vitrectomy probe of claim 6, wherein the endolaser fiber runs coaxially through the cannula.

8. The illuminated vitrectomy probe of claim 6, wherein light can be provided independently to the end-illumination array, the angle-illumination array and the endolaser fiber in any combination.

9. The illuminated vitrectomy probe of claim 1, wherein the array of optical fibers are disposed in a circular pattern around the cannula near the cutting port.

10. The illuminated vitrectomy probe of claim 1, further comprising:
    a coupling for coupling an end of the array of optical fibers to a light source.

11. An illuminated surgical instrument comprising:
    an instrument with a working area located near an end of a cannula, the instrument having a cutting port disposed at the end of the cannula;
    an array of optical fibers terminating near the end of the instrument, the array of optical fibers located adjacent to the instrument and arranged circumferentially around the cannula to encircle the cannula such that the array of optical fibers provides illumination to the working area, the array of optical fibers comprising:
       an end-illumination array of optical fibers configured to provide illumination in a direction along a longitudinal axis of the instrument; and
       an angle-illumination array of optical fibers, each fiber having a covered terminal distal end to prevent light emission from the terminal distal end, one or more of the fibers being free from cladding to form an aperture along the radial surface of the illuminated surgical instrument to allow light emission from the aperture in order to provide illumination in a direction at an angle to the longitudinal axis of the instrument, the illumination of the angle-illumination array being at an angle relative to the illumination of the end-illumination array.

12. The illuminated surgical instrument of claim 11, wherein the plurality of optical fibers and instrument are configured to fit through the cannula with a size not greater than 23-gauge.

13. The illuminated surgical instrument of claim 11, further comprising:
    a potting substance that holds the plurality of optical fibers against the instrument.

14. The illuminated surgical instrument of claim 11, further comprising:
    a sleeve that holds the plurality of optical fibers against the instrument.

15. The illuminated surgical instrument of claim 11, wherein the array of optical fibers is arranged to provide targeted illumination to the working area of the instrument and the targeted illumination is configured for an orientation of the working area.

16. The illuminated surgical instrument of claim 11, further comprising an endolaser fiber configured to provide laser light from a laser light source to a surgical site.

17. The illuminated surgical instrument of claim 16, wherein the endolaser fiber runs coaxially through the instrument.

18. The illuminated surgical instrument of claim 16, wherein light for illumination can be provided independently to the end-illumination array, the angle-illumination array and the endolaser fiber in any combination.

19. The illuminated surgical instrument of claim 11, further comprising:
   a coupling for coupling an end of the array of optical fibers to a light source.

* * * * *